US011548836B2

United States Patent
Al-Qasim et al.

(10) Patent No.: US 11,548,836 B2
(45) Date of Patent: Jan. 10, 2023

(54) $CO_2$ UTILIZATION IN MOLTEN SALT REACTOR (MSR) FOR ULTRA ENERGY EFFICIENCY AND REDUCED EMISSIONS

(71) Applicant: SAUDI ARABIAN OIL COMPANY, Dhahran (SA)

(72) Inventors: Abdulaziz S. Al-Qasim, Dammam (SA); Yuguo Wang, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 92 days.

(21) Appl. No.: 17/149,937

(22) Filed: Jan. 15, 2021

(65) Prior Publication Data
US 2022/0227683 A1 Jul. 21, 2022

(51) Int. Cl.
*C07C 1/04* (2006.01)
*C01B 32/50* (2017.01)
(Continued)

(52) U.S. Cl.
CPC .............. *C07C 1/0485* (2013.01); *C01B 3/34* (2013.01); *C01B 32/50* (2017.08);
(Continued)

(58) Field of Classification Search
CPC ....... C01B 3/34; C01B 32/50; C01B 2203/86; C07C 29/1518; C07C 1/0485; C25B 1/04; C10G 2/50
See application file for complete search history.

(56) References Cited

U.S. PATENT DOCUMENTS 7,163,758 B2 1/2007 Steinberg
8,277,632 B2 10/2012 Murahara
(Continued)

FOREIGN PATENT DOCUMENTS

EP 0497226 A2 8/1992
EP 2817438 A2 12/2014
(Continued)

OTHER PUBLICATIONS

International Search Report issued in corresponding International Applicaiton No. PCT/US2022/012484, dated May 9, 2022 (3 pages).
(Continued)

*Primary Examiner* — Jafar F Parsa
(74) *Attorney, Agent, or Firm* — Osha Bergman Watanabe & Burton LLP

(57) ABSTRACT

A system for a carbon neutral cycle of gas production may include a molten salt reactor configured to generate zero carbon dioxide ($CO_2$) emissions electricity. The system may include a desalination unit configured to receive the zero-$CO_2$ emissions electricity from the molten salt reactor and produce a desalinated water. The system may include an electrolysis unit configured to be powered by the zero-CO2 emissions electricity generated by the molten salt reactor and generate hydrogen ($H_2$) and oxygen ($O_2$) from the desalinated water. The system may include an oxy-combustion unit configured to receive and combust a hydrocarbon fuel with the $O_2$ from the electrolysis unit to produce electricity and $CO_2$. The system may include a $CO_2$ capture system adapted to capture the $CO_2$ produced by the oxy-combustion unit and a catalytic hydrogenation unit configured to receive and convert $H_2$ from the electrolysis unit and $CO_2$ from the $CO_2$ capture system to produce the hydrocarbon fuel.

8 Claims, 2 Drawing Sheets

(51) Int. Cl.
  *C25B 15/08* (2006.01)
  *C25B 9/17* (2021.01)
  *C01B 3/34* (2006.01)
  *C07C 29/151* (2006.01)
  *C10G 2/00* (2006.01)
  *C25B 1/04* (2021.01)
  *G21C 3/54* (2006.01)
  *G21C 1/22* (2006.01)

(52) U.S. Cl.
  CPC .......... *C07C 29/1518* (2013.01); *C10G 2/50* (2013.01); *C25B 1/04* (2013.01); *C25B 9/17* (2021.01); *C25B 15/081* (2021.01); *G21C 3/54* (2013.01); *C01B 2203/84* (2013.01); *C01B 2203/86* (2013.01); *G21C 1/22* (2013.01)

(56) References Cited

U.S. PATENT DOCUMENTS

| | | | |
|---|---|---|---|
| 10,106,753 | B1 | 10/2018 | Graham et al. |
| 10,208,665 | B2 * | 2/2019 | Simpson ................ C25B 9/73 |
| 2009/0115190 | A1 | 5/2009 | Devine |
| 2010/0320120 | A1 | 12/2010 | Siskin et al. |
| 2015/0159126 | A1 | 6/2015 | Makowsky et al. |
| 2016/0045841 | A1 | 2/2016 | Kaplan et al. |
| 2019/0359894 | A1 | 11/2019 | Heidel et al. |

FOREIGN PATENT DOCUMENTS

| | | |
|---|---|---|
| EP | 3359627 A1 | 8/2018 |
| JP | 2000218129 A | 8/2000 |
| WO | 2016073500 A1 | 5/2016 |
| WO | 2019226416 A1 | 11/2019 |

OTHER PUBLICATIONS

Written Opinion issued in corresponding International Applicaiton No. PCT/US2022/012484, dated May 9, 2022 (5 pages).
Harto, Andang W. and Mella Soelanda, "Mass and Energy Balance Analysis of Methanol Production Using Atmospheric CO2 Capture with Energy Source from PCMSR", E3S Web of Conferences, The Authors, EDP Science, vol. 42, No. 01004, 2018, pp. 1-6 (6 pages).
"Developing the next generation of reactors", Power: News & Technology for the Global Energy Industry, vol. 152, Apr. 2008 (35 pages).
Miguel, Cados V. et al., "Direct CO2 hydrogenation to methane or methanol from postcombustion exhaust streams—A thermodynamic study", Journal of Natural Gas Science and Engineering, ScienceDirect, Elsevier B.V., vol. 22, 2015, pp. 1-8 (8 pages).
"Electrolysis of water", Wikipedia, Access Date: Jan. 14, 2021, URL: <https://en.wikipedia.org/wiki/Electrolysis_of_water> (13 pages).
"Desalination", Wikipedia, Access Date: Jan. 14, 2021, URL: <https://en.wikipedia.org/wiki/Desalination> (17 pages).
"Molten salt reactor", Wikipedia, Access Date: Jan. 14, 2021, URL: <https://en.wikipedia.org/wiki/Molten_salt_reactor> (20 pages).

* cited by examiner

_US 11,548,836 B2_

CO$_2$ UTILIZATION IN MOLTEN SALT REACTOR (MSR) FOR ULTRA ENERGY EFFICIENCY AND REDUCED EMISSIONS

BACKGROUND

As global demand for energy grows, greenhouse gas emissions into the earth's atmosphere also increase. This growth in greenhouse gas emissions disrupts the balance of the Earth's ecosystem and affects all life. Greenhouse gases, particularly carbon dioxide ($CO_2$), undesirably absorb and emit radiation within the atmosphere, causing a "greenhouse effect." Attention to curb greenhouse gases has focused on $CO_2$ emissions due to the ever-increasing combustion processes emitting $CO_2$ as a waste product into the environment.

Lawmakers, worldwide, have also focused their efforts in cutting $CO_2$ emissions by pushing carbon neutrality, legislating the development of new technologies and changing tax, penalty, and incentive programs to cut down on $CO_2$ emissions and develop new carbon neutral integrative processes.

The increase in $CO_2$ emissions has led to the development of Carbon Capture, Utilization and Storage (CCUS). CCUS is a set of technologies that is used to capture carbon dioxide emissions at the source, thus preventing the $CO_2$ from entering the atmosphere. The $CO_2$ emissions are transported away and may be either stored deep underground or turned into useful products. Capturing $CO_2$ has been used to help improve the quality of natural gas. As the field continues to innovate, $CO_2$ may be removed and sequestered indefinitely. Moreover, it may also be turned into a marketable industrial commercial product, thus adding value to an otherwise harmful waste stream.

Accordingly, there exists a need for innovations in carbon (dioxide) capture and storage capabilities.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a system for a carbon neutral cycle of gas production. The system may include a molten salt reactor configured to generate zero carbon dioxide ($CO_2$) emissions electricity. A desalination unit may be provided and configured to receive the zero-$CO_2$ emissions electricity from the molten salt reactor and produce a desalinated water. An electrolysis unit may also be provided and configured to be powered by the zero-$CO_2$ emissions electricity generated by the molten salt reactor and generate hydrogen ($H_2$) and oxygen ($O_2$) from the desalinated water. The system may also include an oxy-combustion unit configured to receive and combust a hydrocarbon fuel with the $O_2$ from the electrolysis unit to produce electricity and $CO_2$. The system may also provide a $CO_2$ capture system adapted to capture the $CO_2$ produced by the oxy-combustion unit and a catalytic hydrogenation unit configured to receive and convert $H_2$ from the electrolysis unit and $CO_2$ from the $CO_2$ capture system to produce the hydrocarbon fuel.

In another aspect, embodiments disclosed herein relate to a method for a carbon neutral cycle of a natural gas production. The method may include generating electricity with a molten salt reactor configured to generate zero carbon dioxide ($CO_2$) emissions. The method may also include powering a desalination unit with the electricity from the molten salt reactor, producing desalinated water ($H_2O$) with the desalination unit. The method may include producing hydrogen ($H_2$) and oxygen ($O_2$) from the desalinated water ($H_2O$) with an electrolysis unit and introducing the $H_2$ produced by the electrolysis unit to a catalytic hydrogenation unit. The method may include reacting captured $CO_2$ and the $H_2$ generated from the desalination unit by catalytic hydrogenation in a catalytic hydrogenation unit, wherein the reaction produces a hydrocarbon fuel. The method may also include introducing the hydrocarbon fuel into an oxy-combustion unit and producing $CO_2$ in the oxy-combustion unit by reacting the hydrocarbon fuel with the $O_2$ from the electrolysis unit. The method may also include capturing $CO_2$ from the oxy-combustion unit and introducing the captured $CO_2$ to the catalytic hydrogenation unit.

Other aspects and advantages of the claimed subject matter will be apparent from the following description and the appended claims.

DETAILED DESCRIPTION

Embodiments of the present disclosure relate to the fields of $CO_2$ utilization and value creation. Embodiments of the present disclosure relate to systems and methods of using green (clean) electrical energy with zero $CO_2$ emissions generated by a molten salt reactor (MSR) to convert $CO_2$ into commercial products for a carbon neutral life cycle.

The capture and conversion of $CO_2$ is useful across industrial and commercial applications, such as the production of methane ($CH_4$) and methanol ($CH_3OH$). Carbon capture and storage is a central part of efforts to achieve net zero $CO_2$ and other greenhouse gas emissions, while also ensuring the world can continue to innovate and thrive. Capturing carbon has been used to help improve the quality of natural gas, but has fallen short of turning $CO_2$ into a marketable industrial and commercial product while also achieving carbon neutrality.

Embodiments of the present disclosure relate to $CO_2$ utilization and value creation. $CO_2$ may be captured and converted into useful industrial products. The driving energy of the $CO_2$ conversion is clean electricity generated with zero $CO_2$ emission operation, such as molten salt reactor operations.

Figure 1:
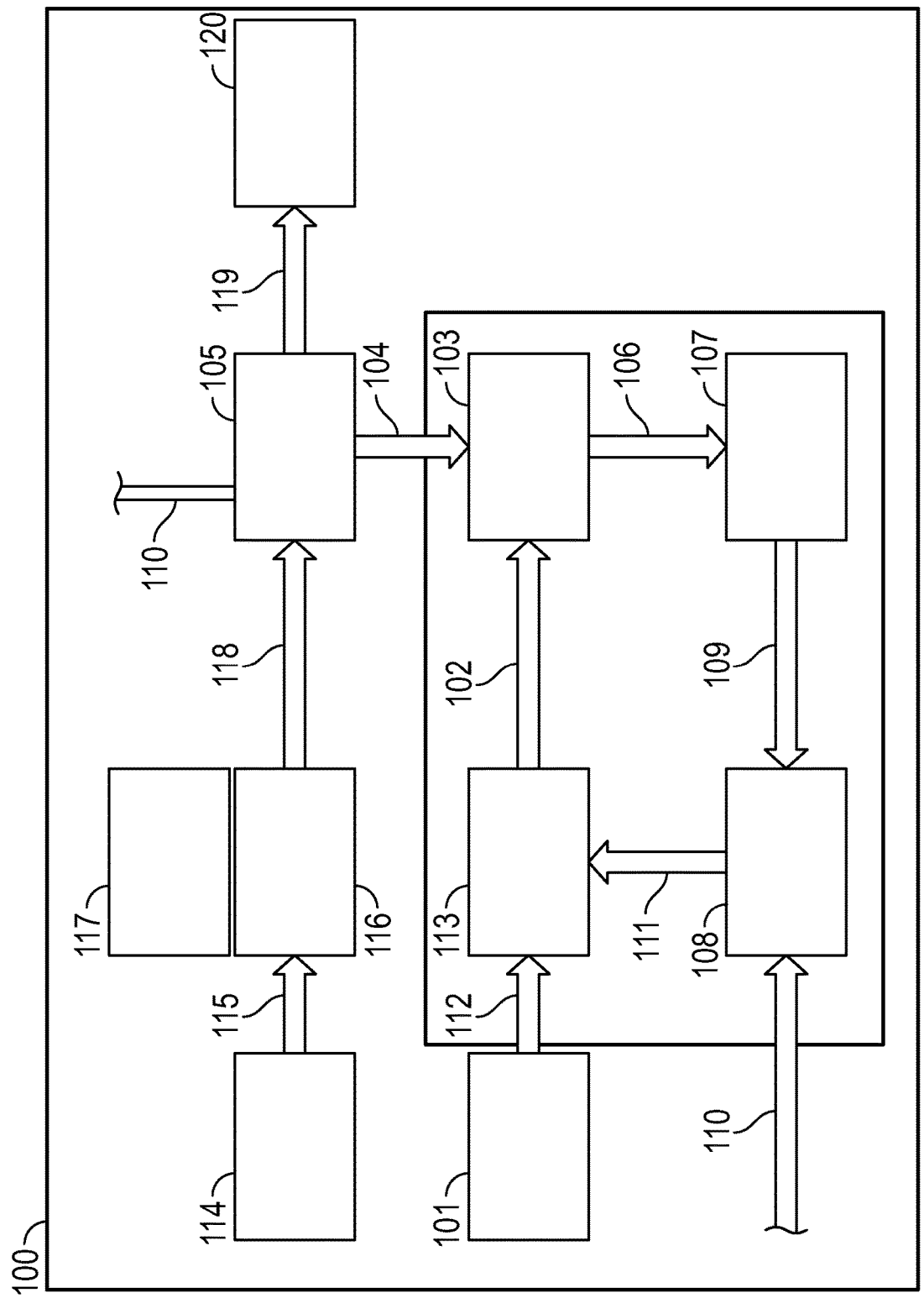
FIG. 1 is a flow diagram of a $CO_2$ utilization and value creation process according to embodiments of the present disclosure.

FIG. 1 shows an embodiment of the overall $CO_2$ utilization and value creation process 100 of the current disclosure. In the embodiment shown in FIG. 1, $CO_2$ may be captured from a natural gas production process 101, such as a natural gas production plant gas sweetening process, and enter line 112. It will be understood by those skilled in the art that $CO_2$ may be captured from other sources, including cement factories, biomass power plants, oil refineries, and other heavy industrial sources, particularly those that burn fossil fuels.

The captured $CO_2$ may be fed into a catalytic hydrogenation unit 103 through line 102. In the catalytic hydrogenation unit 103, hydrogen ($H_2$) may enter in through line 104, wherein it may react with the $CO_2$ from line 102 to produce a hydrocarbon fuel, such as $CH_4$. The $H_2$ may be produced from an electrolysis unit 105 connected to the catalytic hydrogenation unit 103 via line 104. The $CH_4$ may flow through line 106 and into the natural gas grid 107. Although the embodiment shown in FIG. 1 shows the production of $CH_4$, it will be understood by those skilled in the art with the benefit of the current disclosure that other hydrocarbon fuels, such as $CH_3OH$, may be produced in embodiments of the present disclosure.

As shown in FIG. 1, some embodiments may have an oxy-combustion unit 108 fluidly connected to the catalytic hydrogenation unit 103 and the natural gas grid 107 via line 106 and line 109. $CH_4$ may be injected into the oxy-combustion unit through line 109 wherein it may react with oxygen ($O_2$) from line 110 to produce a $CO_2$ stream in line 111. The $O_2$ may be produced in the electrolysis unit 105 connected to the oxy-combustion unit 108 via line 110. The $CO_2$ produced by the oxy-combustion unit 108 and flowing through line 111 may be captured and combined with the $CO_2$ from the natural gas production process 101 flowing though line 112. The combined captured $CO_2$ may be stored in a $CO_2$ storage unit 113 until the $CO_2$ is fed into the catalytic hydrogenation unit 103 via line 102.

It will be understood by those skilled in the art that the captured $CO_2$ from the natural gas production process 101 and the $CO_2$ from the oxy-combustion unit 108 may not be stored in the same storage unit. It will also be understood by those in the art that the captured $CO_2$ from the natural gas production process 101 and the captured $CO_2$ from the oxy-combustion unit 108 may be directly connected to the catalytic hydrogenation unit 103, either separately/independently of each other or through a combined line wherein both captured $CO_2$ streams (line 111 and line 112) fluidly connect in a single line 102 to the catalytic hydrogenation unit 103 (not shown in the FIG. 1 embodiment).

In embodiments of the present disclosure, the combined captured $CO_2$ (as shown stored in $CO_2$ storage unit 113), the $CO_2$ in line 102, the catalytic hydrogenation unit 103, the $CH_4$ in line 106, the natural gas grid 107, the $CH_4$ flowing in line 109, the oxy-combustion unit 108, and the $CO_2$ in line 111, or any combination thereof, may form a carbon neutral natural gas cycle.

In embodiments of the present disclosure, the driving energy of the overall $CO_2$ utilization and value creation process 100 may be electricity generated by a molten salt reactor 114. As shown in FIG. 1, a molten salt reactor 114 may generate electricity. The molten salt reactor 114 may generate clean/green electricity, wherein the molten salt reactor 114 does not release $CO_2$ into the atmosphere. Oxy-combustion unit 108 may also be used to produce electricity, used within the carbon-neutral natural gas cycle (113→103→107→108→113) and/or exported; energy from the oxy-combustion unit 108 may also or additionally be used for other processes requiring radiant or convective heat or transformation into work, such as via a turbine.

In embodiments of the present disclosure, the electricity generated from the molten salt reactor 114 may be used to desalinate seawater. The electricity may flow from the molten salt reactor 114 through line 115 to provide power to the desalination of seawater in desalination unit 116. The high salinity water, brine, and/or salts produced from the desalination unit 116 may be used in an enhanced oil recovery unit 117. The desalination unit 116 may be incorporated into the enhanced oil recovery unit 117, wherein the high salinity water, brine, and/or salts may be injected into oil-bearing reservoirs to maintain the reservoir pressure and improve secondary hydrocarbon recovery. The water ($H_2O$) product stream from the desalination unit 116 may flow through line 118 to an electrolysis process.

As shown in FIG. 1, the $H_2O$ from the desalination unit 116 may flow through line 118 to an electrolysis unit 105. In the electrolysis unit 105, the $H_2O$ may be decomposed into $O_2$ and $H_2$ in an electrolysis reaction. The electrolysis reaction may also be powered by the electricity generated in the molten salt reactor 114. The electrolysis of $H_2O$ in the electrolysis unit 105 may produce an $O_2$ stream in line 110 and a $H_2$ stream in line 104. The $O_2$ stream in line 110 may be connected to the oxy-combustion unit 108 via line 110 wherein it may provide $O_2$ for the oxy-combustion reaction. The $H_2$ stream may be connected to the catalytic hydrogenation unit 103 via line 104 wherein it may provide $H_2$ for the catalytic reaction with $CO_2$ to form a methane product. The $H_2$ produced in the electrolysis of $H_2O$ may also be connected via line 119 to be used in other industrial applications 120, such as refinery applications, fuel cells, and hydrogenation.

In one aspect, embodiments disclosed herein relate to $CO_2$ captured from industrial operations. An example of a source for captured $CO_2$ is a conventional natural gas plant. Natural gas with carbon capture uses post-combustion capture methods. $CO_2$ is a product of burning natural gas. Post-combustion capture of $CO_2$ is a conventionally available integrated operation of natural gas combined cycle plants. Methods of $CO_2$ separation/removal from a natural gas emission may include membrane-based systems and filter systems. The high cost of efficiency penalties associated with carbon capture and storage, as well as methane leakage from natural gas extraction and distribution limit the benefit of carbon capture and storage on reducing greenhouse gases. Some embodiments of the present disclosure may use the captured $CO_2$ of a natural gas production plant in a subsequent, downstream, value-added process to ensure the $CO_2$ is not released into the atmosphere.

In some embodiments of the present disclosure, conventional natural gas plants capture $CO_2$ in a gas sweetening process. Gas sweetening is the process of removing hydrogen sulfides, carbon dioxide, and mercaptans from natural gas to make it suitable for transport and sale. It is desirable to sweeten natural gas because $H_2S$ and $CO_2$ have a corrosive effect on gas pipelines. The $CO_2$ is removed, captured from the pipeline and either stored in facilities or used in processes that use $CO_2$, and not released into the atmosphere as greenhouse gases.

In embodiments of the present disclosure, captured $CO_2$ may be used in a catalytic hydrogenation process. Catalytic hydrogenation of the present disclosure produces methane or methanol from $CO_2$ (from a captured $CO_2$ stream) and $H_2$ (e.g., from an electrolysis process). Catalytic hydrogenation may be used to convert $CO_2$ and $H_2$ into a usable hydrocarbon-based fuel, including methane ($CH_4$) and methanol ($CH_3OH$). The conversion of $CO_2$ into methane or methanol is the prime target reactions in catalytic hydrogenations of the present disclosure, as shown below:

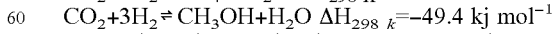

$CO_2 + 4H_2 \rightleftharpoons CH_4 + 2H_2O \quad \Delta H_{298\ K} = -165.0\ kJ\ mol^{-1}$ $CO_2 + 3H_2 \rightleftharpoons CH_3OH + H_2O \quad \Delta H_{298\ K} = -49.4\ kj\ mol^{-1}$ To catalyze the reaction between $CO_2$ and $H_2$, surface sites that bind and activate $CO_2$ need to co-exist and cooperate with sites for dissociation of $H_2$. Activation of $CO_2$ by heterogeneous catalysis is often carried out using conventional reducible oxides, including ceria, zirconia, or titania, while metals are conventionally used to dissociate $H_2$. It is desirable to use a catalyst that can efficiently and effectively suppress the formation of by-products in favor of the formation of methane or methanol.

Hydrogenation of $CO_2$ to methane is thermodynamically favorable over other $CO_2$ conversion reactions. Different transition metals, such as Ru, Rh, Ni, and Pd have been known to be highly selective and active for the methane formation by $CO_2$ hydrogenation, particularly at low temperatures. The supported Ni catalysts conventionally have the highest selectivity to form methane.

Catalytic hydrogenation of $CO_2$ with $H_2$ to produce $CH_4$ and $CH_3OH$ has a wide range of applications, including the production of syngas and the formation of compressed natural gas. It is a key pathway for $CO_2$ recycling and it can offer a solution for renewable $H_2$ storage and transportation. In parallel, the $CO_2$ hydrogenation reactions to produce $CH_4$ and/or $CH_3OH$ are considered to be useful in reclaiming oxygen ($O_2$) within a closed cycle. Catalytic hydrogenation of $CO_2$ to produce $CH_4$ and/or $CH_3OH$ requires substantial amounts of $H_2$.

In embodiments of the present disclosure, the $CO_2$ capture and catalytic hydrogenation unit may be oversized, thus producing a surplus of $CH_4$ and/or $CH_3OH$. This oversized unit may improve the unit operations and efficiency of scale. A portion of the $CH_4$ or $CH_3OH$ product stream from an oversized unit may be fed to a downstream process. For example, in embodiments of the present disclosure, $CO_2$ may be catalytically hydrogenated into $CH_3OH$, wherein the $CH_3OH$ is injected into the natural gas grid. The $CH_3OH$ produced by catalytic hydrogenation may also be injected/fed into an oxy-combustion process to produce electricity. $CH_3OH$, as produced by embodiments of the present invention, may be used as a feedstock for chemicals, such as ethylene or propylene through a methanol to olefin process.

$H_2$ may be produced by a number of processes, but industrially is preferentially produced using non-renewable feedstocks. Hydrogen production is also generally considered an expensive undertaking, particularly with methods such as steam methane reforming.

Steam methane reforming is one of the most commonly used commercialized methods of producing hydrogen. Steam methane reforming produces hydrogen (syngas) by reaction of hydrocarbons with water. The reaction is often conducted under high pressure mixture of steam and methane in the presence of a nickel catalyst. In some steam methane reforming processes, a desulfurized hydrocarbon feedstock (e.g., natural gas) is preheated, mixed with steam and passed over a catalyst to produce carbon monoxide, carbon dioxide, and hydrogen, wherein the hydrogen is subsequently separated. Steam methane reforming accounts for the majority of the worlds produced hydrogen, but is not considered a clean/green resource due to its production of greenhouse gases. Thus, it is desirable to decrease $CO_2$ emissions wherein the $H_2$ necessary for the catalytic hydrogenation is sourced from a clean, renewable resource. An example of a clean resource that produces hydrogen is water electrolysis powered by green energy.

Water electrolysis is considered an effective alternative to steam methane reforming for the production of $H_2$. In embodiments of the present disclosure, electrolysis of $H_2O$ produces the $H_2$ used in the catalytic hydrogenation process. The hydrogen production process in the present disclosure may be connected to an energy source, such as a molten salt reactor, to power the electrolysis reaction.

Figure 2:
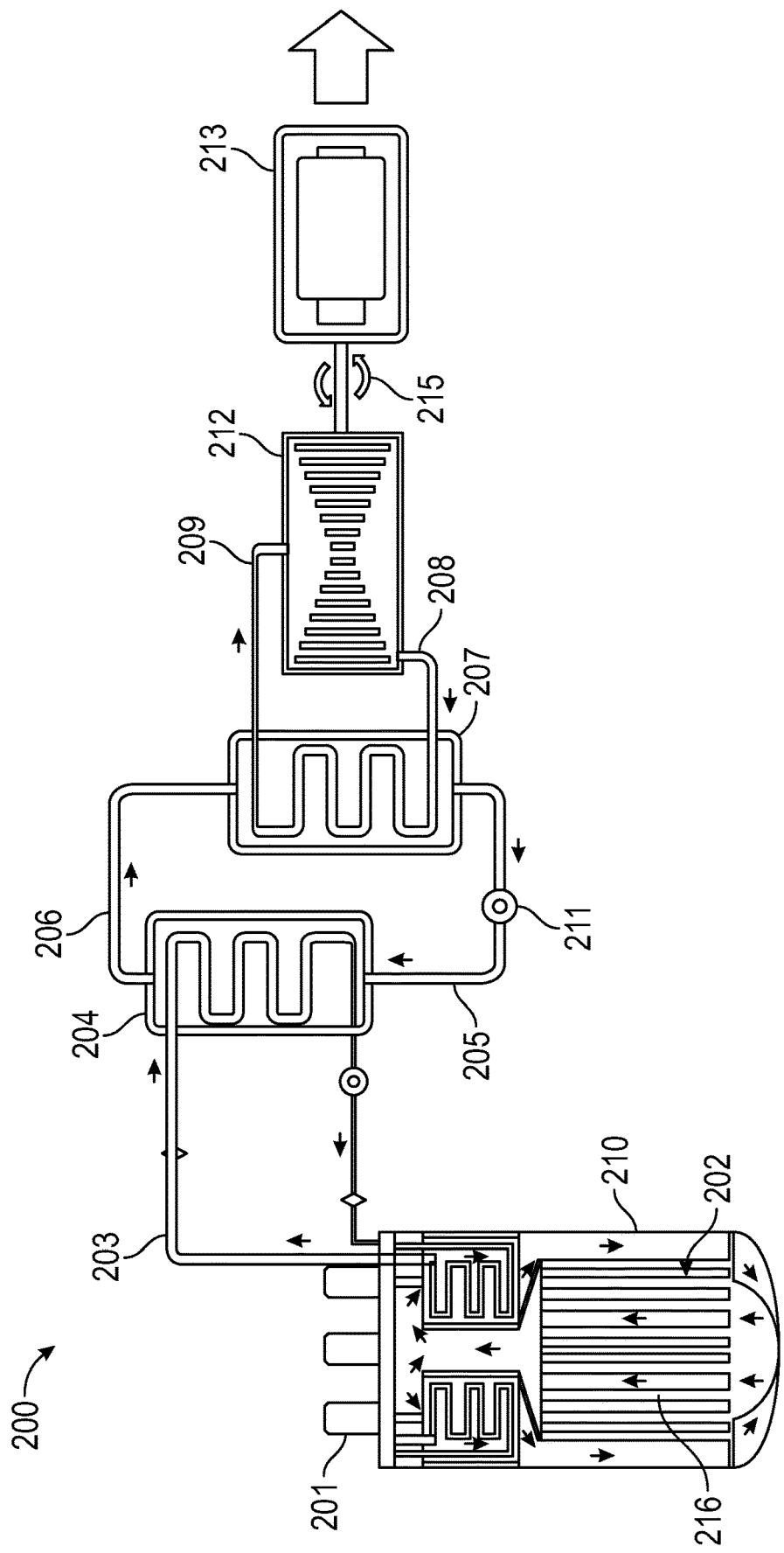
FIG. 2 is a schematic of an exemplary molten salt reactor system.

A molten salt reactor (MSR) is a nuclear fission reactor that uses molten fluoride salts as a primary coolant at low pressure, wherein fissile and fertile fuel may be dissolved in the salt instead of fuel rods. FIG. 2 shows a schematic of an exemplary MSR system 200. As shown in FIG. 2, fuel is dissolved within a fluoride salt mixture, producing either uranium fluoride or thorium fluoride inside a reactor tank 210 and circulated around a reactor core unit 202 via circulation motors 201. The reactor core unit 202 may include a graphite reactor core defining an internal space that houses one or more fuel wedges 216. The fuel salt flows through line 203 to a heat exchanger 204 where it is used to heat solar salt that enters the primary heat exchanger 204 through line 205. The heated solar salt exits the primary heat exchanger 204 through line 206 wherein it enters a steam generator 207. The heat from the solar salt is used to heat water entering the steam generator 207 through line 208. The water is heated under high pressure in the steam generator 207 and exits through line 209 as steam. The cooled solar salt is pumped via salt circulating pump 211 back to heat exchanger 204. The steam from line 209 drives turbine 212 by operations understood by those skilled in the art. The turbine rotates a shaft 215 connected to a generator 213. The generator 213, in turn, converts the mechanical energy to electrical energy based on mechanisms understood by those skilled in the art.

The arrangement and operation of MSRs vary according to design specifications. For example, the use of molten salt as fuel and as coolant are independent design choices. The original circulating-fuel-salt MSR and the more recent static-fuel-salt stable salt reactor use salt as fuel and salt as coolant; a dual fluid reactor uses salt as fuel but metal as coolant; and the fluoride salt-cooled high temperature reactor has solid fuel but salt as coolant.

Although MSRs operate on the same basic principle as other nuclear power reactors (controlled fission to produce steam that powers electricity-generating turbines), MSRs offer advantages over conventional nuclear power plants. As in all low-pressure reactor designs, MSRs achieve passive decay heat removal. In some designs, the fuel and the coolant may be the same fluid, so a loss of coolant removes the reactor's fuel, similar to how loss of coolant also removes the moderator in light water reactions. Unlike steam in alternative reactors, the fluoride salts of MSRs dissolve poorly in water and do not form burnable hydrogen. Also, molten salts are not damaged by the core's neutron bombardment, unlike steel and solid uranium oxide in other reactors.

Some reactors, such as a boiling water reactor (BWR), utilize high pressure radioactive steam that may leak the radioactive steam and cooling water, requiring expensive containment systems, piping, and safety equipment. MSRs advantageously utilize low pressure with a lower risk of leakage. However, most MSR designs require fluid with radioactive fission product in direct contact with pumps and heat exchangers.

Other advantages of MSRs include cheaper closed nuclear fuel cycles because they can operate with slow neutrons. If fully implemented, reactors that close the nuclear fuel cycle may reduce environmental impacts. For example, chemical separation may turn long-lived actinides back into reactor fuel. The MSR fuel's liquid phase might be pyroprocessed to separate fission products (nuclear ashes) from actinide fuels. The discharged wastes generally have shorter half-lives. This reduces the need for geologic containment to 300 years rather than the tens of thousands of years as needed by a light-water reactor's spent nuclear fuel. It also permits the use of alternate nuclear fuels, such as thorium.

It is also notable that fuel rod fabrication is not required in MSRs, as they are replaced with fuel salt synthesis. Some MSR designs are compatible with the fast neutron spectrum, which can pyroprocess problematic transuranic elements like Pu240, Pu241 and up (reactor grade plutonium) from traditional light-water nuclear reactors.

An MSR can react to load changes in less than 60 seconds (unlike "traditional" solid-fuel nuclear power plants that suffer from xenon poisoning). Molten salt reactors can run at high temperatures, yielding high thermal efficiency. This reduces size, expense, and environmental impacts. MSRs can offer a high "specific power," that is high power at a low mass. A possibly good neutron economy makes the MSR attractive for the neutron poor thorium fuel cycle.

A notable advantage of the MSR as a source of energy in embodiments of the present disclosure is that the energy produced by MSR may be considered a green energy, in that it may not produce $CO_2$ emissions. This green energy may be utilized in embodiments of the present disclosure to power desalination of seawater to create $H_2O$, wherein the $H_2O$ is ultimately used to produce the $H_2$ for the catalytic hydrogenation process described above.

Embodiments of the present disclosure may include a desalination process, wherein $H_2O$ may be produced by desalination of seawater (water with dissolved salt and other minerals). Desalination refers to the removal of salts and other minerals from a target substance, like seawater. In desalination, salt water (seawater) is fed into a container. Feed sources may include brackish, seawater, wells, rivers, streams, wastewater, and industrial feed and process waters.

Desalination processes may use membrane separation techniques. Salt water may pass through a semipermeable membrane. The membrane filters the salt and minerals from the salt water, producing $H_2O$ (fresh water). Membrane separation requires a high driving force, including applied pressure, vapor pressure, electric potential, and concentration to overcome natural osmotic pressures and effectively force water through a target membrane. As such, desalination is an energy intensive process. It is conventionally powered by fossil fuel processes, thereby contributing the $CO_2$ emissions. Reverse osmosis (RO) and nanofiltration (NF) are the leading pressure driven membrane processes. Membrane configurations include spiral wound, hollow fiber, and sheet with spiral being the most widely used. Contemporary membranes are primarily polymeric materials with cellulose acetate still used to a much lesser degree. Electrodialysis (ED), electrodialysis reversal (EDR), forward osmosis (RO), and membrane distillation (MD) are also membrane processes used in desalination.

Embodiments of the present disclosure may power the desalination process with the energy generated by a molten salt reactor. As described above, the energy from the MSR in embodiments of the present disclosure may be generated without producing $CO_2$ emissions. By using the energy created by a MSR with zero/negligible $CO_2$ emissions as the driving force for the desalination of seawater instead of conventional methods that burn fossil fuels, less $CO_2$ is released into the atmosphere.

Embodiments of the present disclosure may use the concentrated salt water, brine, and/or salts produced by the desalination in an enhanced oil recovery (EOR) process. The desalination partially or fully removes $H_2O$ from seawater, producing pure water ($H_2O$) and either high salinity water, brine, or salts, depending on the extent of the $H_2O$ removal. EOR may use the high salinity water (or add the salts to water to create high salinity water) in water flooding techniques. Water flooding may be used as a secondary method to improve oil recovery. Oil pressures decline during oil production, leading to a reduction in oil productivity. EOR methods, such as water flooding, inject high-salinity water into target reservoir zones to maintain, support, or increase the reservoir pressure and oil productivity. The high salinity water and salts produced by the desalination of embodiments of the present disclosure may be used in these EOR.

Embodiments of the present disclosure may use the high salinity, brine, or salts for other industrial applications, such as cooling water for power generation, aquaculture, and for a variety of other uses in the oil and gas industry, such as drilling and hydraulic fracturing.

Embodiments of the present disclosure may use the $H_2O$ produced in the desalination process to produce $H_2$ and $O_2$ streams via electrolysis. The $H_2$ produced may be used in the catalytic hydrogenation process and the $O_2$ may be used in an oxy-combustion process. Electrolysis (i.e., water-splitting) of $H_2O$ produces $H_2$ and $O_2$ from renewable resources by using electricity to split water molecules. Electrolysis may occur in a vessel called an electrolyzer. The electrolyzer may be configured to house an anode and a cathode. The anode and cathode may be connected to power source. $H_2$ will form at the cathode and $O_2$ will form on the anode.

In some embodiments, the anode and cathode may be separated by an electrolyte. The efficiency of the electrolysis process may be increased through the addition of an electrolyte, as well as the use of an electrocatalyst. Electrolyzers may function in different ways depending on the type of electrolyte material used in the process. Examples of different electrolyzers include polymer electrolyte membrane electrolyzers, alkaline electrolyzers, and solid oxide electrolyzers. The electrolysis process may be scaled depending on production facility requirements.

$H_2$ produced via electrolysis may result in zero greenhouse gas emissions, depending on the source of the electricity used. The source of the required electricity, the electricity cost and efficiency, as well as emissions resulting from electricity generation must be considered when evaluating the benefits and economic viability of hydrogen production via electrolysis. In embodiments of the present invention, the electricity from the MSR may drive the electrolysis process, resulting in zero/negligible $CO_2$ emissions when producing the hydrogen and oxygen.

In embodiments of the present disclosure, the hydrogen produced via electrolysis may be used in the catalytic hydrogenation process with $CO_2$ to produce $CH_4$ and $CH_3OH$. $CH_4$ and $CH_3OH$ are considered valuable industrial products and fuels. Other applications for the $H_2$ produced in the electrolysis reaction may include refinery hydrogenation operations and other hydrogen economy applications, such as fuel cell powered devices (e.g., cars).

$O_2$ is also a product of electrolysis. In embodiments of the present disclosure, the $O_2$ produced by the electrolysis process is fed into an oxy-combustion process. In the oxy-combustion process, a fossil fuel, such as $CH_4$, is burned in the presence of $O_2$ instead of air to produce $CO_2$, $H_2O$ (water vapor), and electricity. $O_2$ increases combustion efficiency and the concentration of $CO_2$ in flue gasses, thereby improving $CO_2$ capture. The $H_2O$ may be condensed through cooling and the $CO_2$ stream may be captured. The increased $CO_2$ concentration in flue gas may enable the capture of $CO_2$ with a reduced NOx (nitrogen oxides) emission due to the purity of the $O_2$ feed from the $O_2$ produced by the electrolysis process. In the oxy-combustion process of embodiments of the present disclosure, $CH_4$ is fed to the oxy-combustion process and reacted with $O_2$ to create $CO_2$. The oxy-combustion reaction in embodiments of the present disclosure is shown below:

$$CH_4 + 2O_2 \rightarrow CO_2 + 2H_2O$$

The source of $CH_4$ may include the $CH_4$ produced in the catalytic hydrogenation unit, $CH_4$ from a natural gas grid, and a combination of both the $CH_4$ produced in the catalytic hydrogenation unit and natural gas grid.

In embodiments of the present disclosure, $CH_3OH$, and not $CH_4$, may be produced in the catalytic hydrogenation unit and fed into the oxy-combustion unit to produce electricity. In the embodiments that produce $CH_3OH$, the $O_2$ from the electrolysis unit reacts with the $CH_3OH$ in the oxy-combustion unit to produce $CO_2$, $H_2O$ (water vapor), and electricity. The oxy-combustion reaction of the methanol reaction with $O_2$ is shown below:

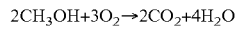
$$2CH_3OH + 3O_2 \rightarrow 2CO_2 + 4H_2O$$

In embodiments of the present disclosure, the $CO_2$ from the oxy-combustion reaction may be captured. The captured $CO_2$ from the oxy-combustion reaction may be stored with the $CO_2$ captured from the natural gas plant. The combined captured $CO_2$ streams may thereby be fed to the catalytic hydrogenation process, wherein it is reacted with the $H_2$ to create $CH_4$ or $CH_3OH$. It will be appreciated by those skilled in the art and the benefit of the present disclosure that the production of $CH_4$ or $CH_3OH$ using embodiments of the present disclosure may be a design choice and depend on the industrial application utilizing embodiments of the present disclosure.

Embodiments of the overall $CO_2$ utilization and value creation process of the current disclosure may capture and process $CO_2$ using clean energy to reduce $CO_2$ emissions in industrial operations. In embodiments of the current disclosure, $CO_2$ captured from industrial processes, such as natural gas sweetening processes, may be combined with $CO_2$ produced by an oxy-combustion reaction to produce $CO_2$ for a catalytic hydrogenation process. The catalytic hydrogenation process may produce either $CH_4$ or $CH_3OH$ by reacting the $CO_2$ with $H_2$. The $CH_4$ or $CH_3OH$ may be fed into a natural gas grid and is in fluid communication with the oxy-combustion process, wherein the $CH_4$ or $CH_3OH$ may react with $O_2$ to produce the $CO_2$ that combines with the $CO_2$ captured from an industrial process. The cycle comprising the $CO_2$ streams (both captured $CO_2$ and $CO_2$ produced by the oxy-combustion process), the catalytic hydrogenation, the natural gas grid, and the oxy-combustion process is exemplary of a carbon neutral natural gas cycle according to embodiments of the current disclosure.

According to embodiments of the current disclosure, the driving energy for the $CO_2$ utilization and value creation process may be energy produced by a MSR. The energy produced by a MSR may be used in a desalination process to produce $H_2O$. The $H_2O$ produced in the desalination process may produce $H_2$ and $O_2$ through electrolysis of the $H_2O$. The $O_2$ from the electrolysis process may be used in the oxy-combustion process of the carbon neutral natural gas cycle. The $H_2$ from the electrolysis may be used in the catalytic hydrogenation of the carbon neutral natural gas cycle, as well as other industrial applications. Embodiments of the present disclosure may provide an option of using clean electrical energy produced, for example, by a molten salt reactor (nuclear) with zero $CO_2$ emission, to convert $CO_2$ into commercial products for a carbon neutral life cycle use of natural gas.

Green (clean) electricity/energy, as defined herein, means energy produced with minimum environmental impact. It is representative of energy resources and technologies that provide the highest environmental benefit, while minimizing environment harm. The U.S. market defines green power/electricity as electricity produced from solar, wind, geothermal, biogas, eligible biomass, and low-impact small hydroelectric sources. It may be synonymous with other terms, such as renewable energy, clean energy, and green energy.

Embodiments of the present disclosure may decrease the $CO_2$ emissions into the atmosphere by a system and process powered by clean/green energy. The driving energy of embodiments of the present disclosure may be green/clean energy generated by a molten salt reactor. The molten salt reactor may have negligible to no measurable $CO_2$ emissions. The $O_2$ in the oxy-combustion process according to embodiments of the present disclosure and the hydrocarbon fuel produces $CO_2$ that may otherwise be released into the atmosphere. The $CO_2$ produced by the oxy-combustion reaction may be combined with $CO_2$ from natural gas production, wherein it is captured and reacted with $H_2$ to produce product streams, such as $CH_4$, $CH_3OH$, or other chemicals (e.g., ethylene and propylene).

The water produced in the desalination process may be used for a variety of applications. The desalination process of the present disclosure, powered by the green/clean energy generated by a molten salt reactor, may produce pure $H_2O$ that may be used for human consumption and industrial applications.

Embodiments of the present disclosure may provide a carbon neutral cycle for the world's future circular carbon economy. Some embodiments of the present disclosure form a carbon neutral gas cycle of natural gas production, $CO_2$ capture, $CO_2$ utilization, $CO_2$ value creation, and $CO_2$ transportation, all powered with clean/green energy generated from a zero $CO_2$ emission molten salt reactor. Examples of $CO_2$ value creation in embodiments of the present disclosure include the production of methane, methanol, methanol, hydrogen, and oxygen. The production of methane and methanol require extensive amounts of hydrogen. According to embodiments of the present disclosure, the hydrogen may be produced by electrolysis of water, the electrolysis process powered by the zero $CO_2$ emission MSR.

Embodiments of the present disclosure decrease $CO_2$ emissions in the production of methane and methanol by producing the hydrogen necessary to produce methane and methanol using clean resources. These clean resources may be desalination and electrolysis powered by a source with zero $CO_2$ emissions, such as a molten salt reactor.

Embodiments of the present disclosure may reduce emission of NOx, by integrating an oxy-combustion process for natural gas power plants, as described above.

Embodiments of the present disclosure may increase potable water production, improve refinery operations, improve hydrogen economic activities with the use of green energy, and increase oil recovery by supporting EOR operations with high-salinity fluids. Excess methane or methanol produced in the carbon neutral natural gas cycle may be exported or converted into other useful products. Similarly, excess hydrogen and oxygen not used in the carbon neutral natural gas cycle may be exported for other industrial or commercial uses.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A method for a carbon neutral cycle of a natural gas production, the method comprising:
    generating electricity with a molten salt reactor configured to generate zero carbon dioxide ($CO_2$) emissions;
    powering a desalination unit with the electricity from the molten salt reactor;
    producing desalinated water ($H_2O$) with the desalination unit;
    producing hydrogen ($H_2$) and oxygen ($O_2$) from the desalinated water ($H_2O$) with an electrolysis unit;
    introducing the hydrogen produced by the electrolysis unit to a catalytic hydrogenation unit;
    reacting captured $CO_2$ and the hydrogen generated from the desalination unit by catalytic hydrogenation in a catalytic hydrogenation unit, wherein the reaction produces a hydrocarbon fuel;
    introducing the hydrocarbon fuel into an oxy-combustion unit;
    producing $CO_2$ in the oxy-combustion unit by reacting the hydrocarbon fuel with the oxygen from the electrolysis unit;
    capturing $CO_2$ from the oxy-combustion unit; and
    introducing the captured $CO_2$ to the catalytic hydrogenation unit.

2. The method of claim 1, wherein the hydrocarbon fuel comprises methane.

3. The method of claim 1, wherein the hydrocarbon fuel comprises methanol.

4. The method of claim 1, wherein the desalination unit produces a high salinity product, the method further comprising using the high salinity product in an enhanced oil recovery process.

5. The method of claim 1, further comprising capturing $CO_2$ sequestered from a natural gas production unit and/or capturing $CO_2$ from a raw or partially processed natural gas stream and combining it with the captured $CO_2$.

6. The method of claim 1, further comprising outputting at least a portion of the hydrogen produced by the electrolysis unit to a refinery and/or a hydrogen capture system for recovering the hydrogen as a product.

7. The method of claim 1, further comprising outputting at least a portion of the hydrocarbon fuel produced by the catalytic hydrogenation unit as a product.

8. The method of claim 1, further comprising feeding a portion of the hydrocarbon fuel to a downstream conversion process.

* * * * *